United States Patent [19]

Tuba et al.

[11] Patent Number: 5,583,138

[45] Date of Patent: Dec. 10, 1996

[54] 17β-SUBSTITUTED 4-AZAANDROSTANE DERIVATIVES, PHARMACEUTICAL COMPOSITIONS CONTAINING THEM AND PROCESS FOR PREPARING SAME

[75] Inventors: Zoltán Tuba; Judit Horváth, both of Budapest; László Kollár, Veszprém; Mária Lovas née Marsai, Budapest; Gábor Balogh, Budapest; Attila Csehi, Göd; András Jávor, Budapest; György Hajoós, Budapest; László Szporny, Budapest, all of Hungary

[73] Assignee: Richter Gedeon Vegyeszeti Gyar Rt., Budapest, Hungary

[21] Appl. No.: 406,920

[22] PCT Filed: Oct. 1, 1993

[86] PCT No.: PCT/HU93/00058

§ 371 Date: Mar. 23, 1995

§ 102(e) Date: Mar. 23, 1995

[87] PCT Pub. No.: WO94/07909

PCT Pub. Date: Apr. 14, 1994

[30] Foreign Application Priority Data

Oct. 2, 1992 [HU] Hungary .................. 92 03135

[51] Int. Cl.⁶ .................................................. A61K 31/58
[52] U.S. Cl. .......................... 514/284; 514/183; 514/212; 540/597; 540/481; 546/77
[58] Field of Search ..................... 540/597, 481; 514/284, 212, 183; 546/77

[56] References Cited

U.S. PATENT DOCUMENTS

| | | | |
|---|---|---|---|
| 4,220,775 | 2/1980 | Rasmussen et al. | 546/77 |
| 4,377,584 | 3/1983 | Rasmussan et al. | 546/77 |
| 4,885,289 | 12/1989 | Breuer | 514/170 |
| 5,304,562 | 4/1994 | Biogaz | 546/77 |
| 5,312,984 | 5/1994 | Nicholas | 564/132 |
| 5,410,040 | 4/1995 | Tuba et al. | 540/96 |
| 5,418,238 | 5/1995 | Panzeri | 514/284 |

FOREIGN PATENT DOCUMENTS

| | | |
|---|---|---|
| 0155096 | 9/1985 | European Pat. Off. . |
| 0200859 | 11/1986 | European Pat. Off. . |
| 0271220 | 6/1988 | European Pat. Off. . |
| 0277002 | 8/1988 | European Pat. Off. . |
| 0285383 | 10/1988 | European Pat. Off. . |
| 0285382 | 10/1988 | European Pat. Off. . |
| 0367502 | 5/1990 | European Pat. Off. . |
| 0462662 | 12/1991 | European Pat. Off. . |
| 0484094 | 5/1992 | European Pat. Off. . |
| 3607651A1 | 9/1987 | Germany . |
| WO91/12261 | 8/1991 | WIPO . |
| 94-07909 | 4/1994 | WIPO ................... 546/77 |
| 95-00531 | 1/1995 | WIPO ................... 546/77 |
| 95-00532 | 1/1995 | WIPO ................... 546/77 |

OTHER PUBLICATIONS

Stinson, Chem & Eng News 29 Jun. 1992 pp. 7–8.
Hellikeer, Wall St. Jour. 7 Jun. 1991 pp. A1, A7.
Diani et al. Jour. Clin. Endo. & Metab., vol. 74, pp. 345–350 (1992).
Frye, et al. J. Med Chem vol. 36 pp. 4313–4315 (1993).
Kuttenn et al. J. Endocr. (1977), vol. 75, 83 to 91.
Sansong et al. J. Invest. Dermatol, vol. 56, 366–372, (1971).
Siiteri et al. J. Clin. Invest., vol. 49, 1737–1745, (1970).
Rittmaster Clin. In. Dermatol. vol. 6, 122–128, (1988).
Liang et al. J. Steroid Biochem., vol. 19, 385–390 (1983).
Rasmusson, Jour. Med. Chem. vol. 29 pp. 2298–2315 (1986).
Back, J. Org. Chem., 1981, 46, 1442 to 1446.
Rasmusson J. Med. Chem., 1984, 27, 1690 to 1701.
Solomons J. Pharm. Sci., 63, 1974, 19 to 23.
Battacharya Synthetic Communications, 30(17), 2683 to 2690 (1990).
Brooks Steroids 47/1, Jan. 1986, 1 to 19.
Winslow, Wall St. Jour., May 7, 1996 p. B4.

*Primary Examiner*—Donald G. Daus
*Attorney, Agent, or Firm*—Herbert Dubno; Jonathan Myers

[57] ABSTRACT

The invention relates to novel 17β-substituted 4-azaandrostane derivatives of general formula (I),

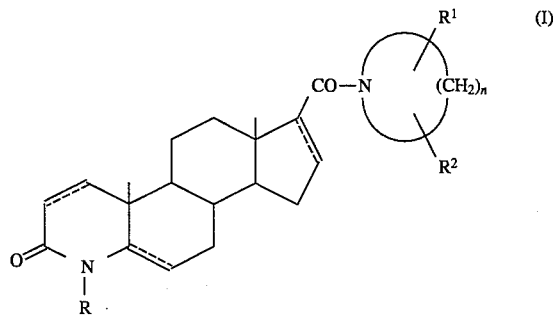

wherein
R means hydrogen or a $C_{1-3}$alkyl group;
$R^1$ and $R^2$ are the same or different and stand for hydrogen or a $C_{1-4}$alkyl group with the proviso that both can mean hydrogen only in the case when n is higher than 5; or
$R^1$ and $R^2$ together means an α,ω-alkylene group containing 5 to 7 carbon atoms, the terminal carbon atoms of said alkylene group being bound to the same ring carbon atom;
n is 4, 5, 6 or 7; and
--- bond line represents a single or double bond.

Furthermore, the invention relates to pharmaceutical composition containing these compounds as well as a process for the preparation of the compounds of general formula (I).

The compounds of general formula (I) exert a 5α-reductase enzyme-inhibiting effect and therefore, they are useful for treating all diseases, where the aim is to reduce the tissue dihydrotestosterone level, such as the benign prostatic hyperplasia, acne, seborrhoea, female hirsutism or androgenic alopecia.

5 Claims, No Drawings

17β-SUBSTITUTED 4-AZAANDROSTANE DERIVATIVES, PHARMACEUTICAL COMPOSITIONS CONTAINING THEM AND PROCESS FOR PREPARING SAME

SPECIFICATION

The invention relates to novel 17β-substituted 4-azaandrostane derivatives of formula (I),

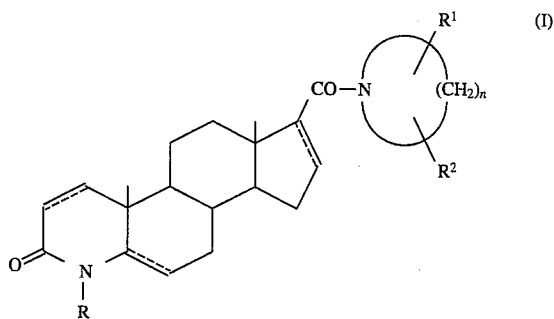

wherein

R means hydrogen or a $C_{1-3}$alkyl group;

$R^1$ and $R^2$, are the same or different and stand for hydrogen or a $C_{1-4}$alkyl group with the proviso that both can mean hydrogen only in the case when n is higher than 5; or $R^1$ and $R^2$ together means an α,ω-alkylene group containing 5 to 7 carbon atoms, the terminal carbon atoms of said alkylene group being bound to the same ring carbon atom;

n is 4, 5, 6 or 7; and

--- bond line represents a single or double bond as well as pharmaceutical compositions containing these compounds.

Furthermore, the invention relates to a process for the preparation of the above compounds and compositions.

The compounds of the formula (I) according to the invention are new and possess a valuable biological activity namely, by inhibiting the function of the 5α-reductase enzyme, they impede the transformation of testosterone to dihydrotestosterone.

Accordingly, the invention relates also to a method of treatment, which comprises administering a therapeutically effective amount of a compound of the formula (I) to a patient to be treated including humans for inhibiting the 5α-reductase enzyme.

BACKGROUND OF THE INVENTION

Among the steroid hormones, the androgens are reponsible for all the physical characteristics distinguishing male individuals from the female ones. In male individuals two steroids, testosterone and its reduced metabolite, i.e. dihydrotestosterone (abbreviated: DHT) are primarily responsible for the androgenic effects. In the tissues of mammals, the transformation of testosterone into DHT is catalyzed by the steroid 5α-reductase enzyme in the presence of nicotinamide adenine dinucleotide phosphate (NADPH). In male individuals, testosterone is predominantly synthetized by the testicles, wherefrom it is carried to the various tissues by the blood flow. In a part of the androgen-sensitive tissues where a significant activity of the steroid 5α-reductase enzyme can be detected, e.g. in the prostatic and skin tissues, the direct mediator of the androgenic effect is dihydrotestosterone which is synthetized in situ from testosterone taken up from the blood flow.

The increase of the DHT concentration in the tissues plays a role in the development and persistence of a number of androgen-dependent diseases, such as e.g. benign prostatic hyperplasia, acne, seborrhea, female hirsutism and androgenic alopecia [J. Clin. Invest. 49, 1737 (1970); J. Invest. Dermatol. 56, 366 (1971); J. Endocr. 75, 83 (1977); as well as Clin. in Dermatol. 6, 122 (1988)]. All substances inhibiting the steroid 5α-reductase enzyme and thereby diminishing the concentration of DHT in the tissues, may be useful for the treatment of the above DHT-dependent diseases.

Based on this recognition, research was directed to the synthesis of 5α-reductase enzyme inhibitors. In the last fifteen years many 5α-reductase enzyme inhibitors containing the steroid skeleton have been described in the literature.

The largest group of 5α-reductase inhibitors known until now is represented by the 4-aza-17-carbamoyl steroids.

A compound containing the 4-aza structural moiety is described in the U.S. Pat. No. 4,377,584 and in J. Steroid Biochem. 19, pages 385 to 390 (1983).

The synthesis of 17β-(N,N-diethylcarbamoyl)-4-methyl-4-aza-5α-androstan-3-one is emphasized in the U.S. Pat. No. 4,220,775. On the basis of literature data this compound was subjected to a comprehensive biological study.

The synthesis of novel 17β-(N-monosubstituted carbamoyl)-4-aza-5α-androstenones, e.g. 17β-[N-(1,1-dimethylethyl)carbamoyl]-3-oxo-4-aza-5α-androst-1-ene [compound of code No. MK-906, named Finasteride] is described in the European patent specification No. 155,096. Nowadays, the above compound has been accepted for therapeutical use.

The synthesis of oxidized analogues of 17β-(N-monosubstituted carbamoyl)-4-aza-5α-androstan-3-one derivatives are published in the European patent specification No. 271,220. It is characteristic of the compounds described that the alkyl substituent of the 17β-(N-monosubstituted carbamoyl) moiety may bear a hydroxyl, carboxyl or alkoxycarbonyl group.

The synthesis and use for the treatment of alopecia of 17β-(N-monosubstituted carbamoyl)-4-aza-5α-androst-1-en-3-one derivatives are described in the European patent specification No. 285,382; whereas the use of the above compounds for the treatment of prostate carcinoma is suggested in the European patent specification No. 285,383.

A novel process for building-up the aminocarbonyl side chain in position 17 of 17β-substituted-3-oxo-4-azasteroids via the Grignard reaction of the imidazole derivative of the appropriate carboxylic acid is presented in the European patent specification No. 367,502.

The European patent specification No. 462,662 discloses the synthesis of 17β-(N-monosubstituted adamantylcarbamoyl)- as well as (norbornylcarbamoyl)-4-aza-5α-androst-1-en-3-one and -4-aza-5α-androstan-3-one. In the patent specifications, the possibilities of use of the 5α-reductase-inhibiting compounds are also discussed.

The synthesis of 4-azasteroids containing double bond(s) in the positions 8(14), 7(8) or 16(17) and/or 1(2) is described in the European patent specification No. 277,002. A characteristic structural moiety of the $C_{17}$-side chain is the aminocarbonyl group, but another side chain containing oxygen or nitrogen may also be present in position 17.

The combination of aromatase inhibitors with 5α-reductase inhibitors is suggested for the treatment of prostatic hyperplasia in the German patent specification No. 3,607, 651. 1-Methylandrosta-1,4-diene-3,17-dione as aromatase inhibitor and 17β-(N,N-diethylcarbamoyl)-4-methyl-4-aza-5α-androstan-3-one as 5α-reductase inhibitor are recommended.

The topical usability of 5α-reductase inhibitors is suggested in the U.S. Pat. No. 4,885,289.

In the PCT patent application published under No. WO 91/12261, the synthesis of 4-azasteroids is disclosed, the $C_{17}$-side chain of which is different from those previously described. A characteristic example of these compounds is 4-methyl-17β-[N-isopropyl-N-(N,N-diisopropylcarbamoyl-)carbamoyl]-4-aza-5α-androstan-3-one.

The synthesis of novel 4-azasteroids bearing a $C_{17}$-side chain of formula —X—COZ is published in the European patent specification No. 200,859. In this formula X means a chemical bond or a straight or branched $C_{1-6}$ aliphatic chain and Z stands for an alkoxy or a substituted amino group. These compounds may contain also an oxo group in position 12 of the steroid skeleton.

The Hungarian patent application No. 3396/91 (published under No. T/59417) relates to the synthesis of 4-azasteroid derivatives containing a $C_{17}$-aminocarbonyl side chain bearing an alkyl group substituted by an aromatic group. These compounds are useful for the treatment and prevention of prostatic hypertrophia.

Various types of azasteroids mainly inhibiting 5α-reductase is summarized in J. Med. Chem. 27, pages 1690 to 1701 (1984). This summary contains biological data, too.

The structure-activity relationship of 5α-reductase inhibitors containing the 4-aza structural moiety is discussed in J. Med. Chem. 29, pages 2298 to 2315 (1986).

The 5α-reductase-inhibiting activity and the biological effect of antiandrogenic properties of 4-azasteroids observed on rats are summarized in Steroids 47/1, pages 1 to 19 (1986).

The transformation of acylimidazole derivatives, mainly to carboxamide derivatives is published in Synt. Comm. 30(17), pages 2683 to 2960 (1990).

The high number of the above-cited literature and patent documents also support the importance of 5α-reductase inhibitors.

OBJECT OF THE INVENTION

The object of the present invention is to prepare new compounds, which show a higher biological effectivity in comparison to those known from the prior art and/or exert a more selective inhibitory effect on the activity of the 5α-reductase enzyme. Namely, the properties mentioned above may result in a more advantageous therapeutical utilization than the known drugs.

SUMMARY OF THE INVENTION

It has surprisingly been found that the 5α-reductase-inhibiting action can significantly be enhanced by the specific selection of the aminocarbonyl substituent in position 17 of 17β-substituted 4-azaandrostene and -androstane derivatives of formula (I) according to the present invention.

According to the invention the preparation of the novel compounds of general formula (I) comprises reacting a 17-halogeno-4-azaandrostene derivative of general formula (II)

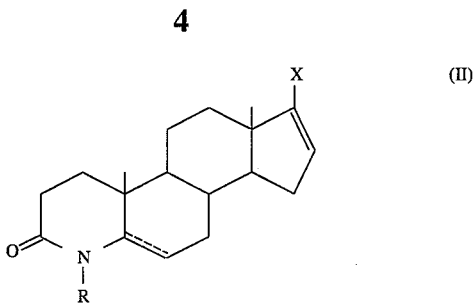

wherein the and ---- bond line are as defined above and X stands for chlorine, bromine or iodine, with a cyclic amine of general formula (III),

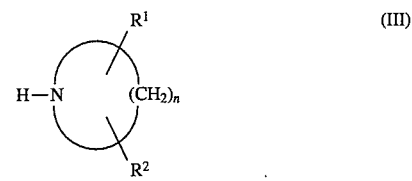

wherein $R^1$, $R^2$ and n are as defined above, in a dipolar aprotic solvent in the presence of a palladium(II) salt, a tertiary amine base and phosphines, or in the presence of a palladium(II) complex and a tertiary amine base, in a carbon monoxide atmosphere at a temperature between 35° C. and 80° C.; and if desired, dehydrogenating an obtained compound of the formula (I), wherein R, $R^1$, $R^2$, the ---- bond line between the $C_5$ and $C_6$ atoms as well as n are as defined above, containing a double bond between the $C_{16}$ and $C_{17}$ atoms as well as a single bond between the $C_1$ and $C_2$ atoms to obtain a compound of the formula (I) containing double bonds between the $C_1$ and $C_2$ atoms as well as between $C_{16}$ and $C_{17}$ atoms, wherein R, $R^1$, $R^2$, the ---- bond line between $C_5$ and $C_6$ atoms and n are as defined above; and/or if desired, transforming by catalytical hydrogenation an obtained compound of the formula (I), wherein R, $R^1$, $R^2$, n, the ---- bond line between the $C_5$ and $C_6$ atoms as well as between the $C_1$ and $C_2$ atoms are as defined above, containing a double bond between the $C_{16}$ and $C_{17}$ atoms, to obtain a compound of the formula (I) containing a single bond as the ---- bond line wherein R, $R^1$, $R^2$ and n are as defined above; and/or if desired, dehydrogenating an obtained compound of the formula (I), wherein R, $R^1$, $R^2$ and n are as defined above, containing single bonds between the $C_1$ and $C_2$ atoms, $C_5$ and $C_6$ atoms, as well as $C_{16}$ and $C_{17}$ atoms, to obtain a compound of the formula (I), containing a double bond between the $C_1$ and $C_2$ atoms, wherein R, $R^1$, $R^2$ and n are as defined above and the ---- bond line means single bonds between the $C_5$ and $C_6$ as well as $C_{16}$ and $C_{17}$ atoms.

In the reaction of the compounds of the formula (II) with the compounds of the formula (III), preferably palladium(II) diacetate or dichloride as palladium(II) salts, triethylamine as a tertiary amine base and triphenylphosphine, 1,4-bis-(diphenylphosphino)butane, 1,2-bis(diphenylphosphino)ethane or 1,3-bis(diphenylphosphino)propane as phosphines are employed. The reaction may be carried out also in such a way that a complex of a palladium (II) salt formed with a phosphine, e.g. [bis(triphenylphosphino)palladium(II)] dichloride or diacetate may be used instead of a palladium(II) salt and phosphines.

In the above reaction, a dipolar aprotic solvent, suitably dimethylformamide or dimethylsulfoxide may be used as solvent.

The compounds of the formula (I) obtained in the above reaction can be subjected to further transformations within the scope of the general formula (I).

Thus, an obtained compound of the formula (I) containing a double bond between the $C_{16}$ and $C_{17}$ atoms and a single bond between $C_1$ and $C_2$ atoms may be dehydrogenated to a compound of the formula (I) containing double bonds both between the $C_1$ and $C_2$ atoms as well as $C_{16}$ and $C_{17}$ atoms.

This dehydrogenation can preferably be performed by using a quinone type substance, e.g. 2,3-dichloro-5,6-dicyano-1,4-benzoquinone in the presence of a silylating agent such as bis(trimethylsilyl)-trifluoroacetamide or with phenylselenic acid anhydride.

Another possibility for the subsequent transformation is provided thereby that an obtained compound, wherein R, $R^1$, $R^2$ and the ---- bond line between the $C_1$ and $C_2$ atoms as well as $C_5$ and $C_6$ atoms and n are as defined above, containing a double bond between the $C_{16}$ and $C_{17}$ atoms can be transformed by catalytic hydrogenation to a compound of the formula (I), containing a single bond as ---- bond line, wherein R, $R^1$, $R^2$ and n are as defined above As another additional transformation, if desired, the thus obtained compounds may be dehydrogenated in the positions 1–2 as described above.

According to a preferred embodiment of the process of the present invention a 17-halogeno-4-azaandrostene derivative of the formula (II) is reacted with an amine of the formula (III), e.g. hexamethyleneimine, heptamethyleneimine, 4-methylpiperidine, 3,3-dimethylpiperidine, 2,6-dimethylpiperidine, 2,5-dimethylpyrrolidine or 3-azaspiro[5,5] undecane in dimethylformamide, in the presence of palladium(II) diacetate, triphenylphosphine and triethylamine under carbon monoxide atmosphere at a temperature of 60° C. for 1.5 to 2 hours.

After the reaction becomes complete, the amines and dimethylformamide are distilled off under reduced pressure. The residue is dissolved in chloroform and successively washed with water, aqueous hydrochloric acid solution, aqueous sodium hydrogen carbonate solution and again with water until neutral. After drying, the solvent is distilled off and the residue is purified by chromatography or recrystallization or by using both methods together.

The obtained 4-aza-17-carboxamido derivatives of the formula (I) containing a double bond between the $C_{16}$ and $C_{17}$ atoms and a single or double bond between the $C_5$ and $C_6$ atoms can be dehydrogenated in the positions 1–2 of the steroid skeleton by using quinones in the presence of a silylating agent or by an other method, e.g. with phenylselenic acid anhydride.

According to the present invention the following procedure is preferably followed. Toluene, 2,3-dichloro-5,6-dicyano-1,4-benzoquinone, bis(trimethylsilyl)-trifluoroacetamide and a catalytic amount of trifluoroacetic acid are added to the compound of the formula (I) to be dehydrogenated. The reaction mixture is stirred under nitrogen at room temperature for 18 hours, meanwhile the progress of the reaction may be followed by liquid chromatography. After disappearance of the starting substance, cyclohexane-1,3-dione is added to the reaction mixture, which is then stirred for an additional 3 hours in order to decompose the excess of 2,3-dichloro-5,6-dicyano-1,4-benzoquinone. Then, the reaction mixture is gently boiled under reflux for 20 hours. During this period the adduct is decomposed and a double bond is formed between the $C_1$ and $C_2$ atoms of the steroid skeleton. To the toluene solution after cooling down, methylene chloride is added and the mixture is stirred with saturated sodium hydrogen carbonate solution. After separating, the organic phase is again extracted with sodium hydrogen carbonate solution. After drying, the solvent is removed under reduced pressure and the residue is purified by recrystallization.

For obtaining saturated compounds of general formula (I), the unsaturated compounds obtained are hydrogenated.

The catalytic hydrogenation may be carried out e.g. in the presence of charcoal supported palladium and hydrogen gas, in alcoholic solution; or in the presence of charcoal-supported palladium catalyst in formic acid medium; or by using platinum(IV) oxide catalyst and hydrogen in glacial acetic acid medium.

In the former case, for example, the unsaturated compound of the formula (I) is dissolved in ethanol and hydrogenated in the presence of charcoal-supported palladium catalyst and hydrogen gas under atmospheric pressure at room temperature. After the reaction becomes complete, the catalyst is filtered off, and after evaporating the solvent the residue is purified by recrystallization.

The double bonds may be saturated also in such a manner that the unsaturated compounds of the formula (I) are dissolved in formic acid and then hydrogenated in the presence of a charcoal supported palladium catalyst; or after dissolving in glacial acetic acid the unsaturated compound may be hydrogenated by using platinum oxide catalyst under hydrogen atmosphere. After filtering off the catalyst, the formic acid or acetic acid used as solvent is distilled off and the residue is purified by recrystallization or chromatography.

By carrying out the hydrogenating and dehydrogenating steps in a suitable succession order compounds of the formula (I) can be prepared, which contain a double bond only between the $C_1$ and $C_2$ atoms. To this purpose, a compound of the formula (I) containing double bond(s), obtained from the reaction of the compounds of the formulae (II) and (III) is saturated by hydrogenation as described above, then the obtained saturated compound of the formula (I) is dehydrogenated in 1–2 positions as described above.

17-Halogeno-4-azaandrostene derivatives of the formula (II) used as starting substances for the preparation of compounds of the formula (I) may be synthetized by using the known 4-aza-5α-androstane-3,17-dione, 4-aza-androst-5-ene-3,17-dione or their N-alkyl derivatives [J. Pharm. Sci. 63, pages 19 to 23 (1974); J. Med. Chem. 27, 1690 (1984); J. Org. Chem. 46, pages 1442 to 1446 (1981)] as follows.

After dissolving the known 4-aza-5α-androstane-3,17-dione, 4-azaandrost-5-ene-3,17-dione or their N-alkyl derivatives, respectively in ethanol, triethylamine and hydrazine hydrate are added to the above solution and the reaction mixture is boiled under reflux. After complete reaction the excess of hydrazine hydrate and triethylamine are distilled off, the residue is precipitated with water, and after filtering off, the precipitate is washed with water until neutral and dried. The thus obtained crude 17-hydrazono derivatives are used after or without purification to prepare the 17-halogeno-4-azaandrostene derivatives of the formula (II).

Compounds of the formula (II) containing iodine as X are prepared in such a way that the 17-hydrazono derivatives obtained in the preceding step are reacted with iodine at room temperature in a halogenated hydrocarbon and/or aromatic solvent in the presence of a tertiary amine base. After complete reaction the tertiary amine base and excess iodine are removed by treatment with dilute aqueous hydrochloric acid solution and then with sodium thiosulfate. After evaporating the solvent, the residue is purified by recrystallization or chromatography.

Compounds of the formula (II) containing chlorine or bromine as X are prepared from the 17-hydrazono derivatives in such a way that the 17-hydrazono derivative is dissolved in pyridine and N-chloro- or N-bromosuccinimide is portionwise added to the above solution at about −10° C. temperature. After complete reaction the crude product is precipitated with water and filtered off. The precipitate is washed until it becomes free from pyridine, then dried and finally purified by recrystallization or chromatography.

The 5α-reductase-inhibiting activity of 4-aza-5α-androstene derivatives of the formula (I) according to the invention was studied by using a standardized in vitro method as follows.

Preparation of the Steroid 5α-reductase Enzyme

Frozen human hyperplastic prostate was used for preparation of the enzyme. The low-frozen prostate was thawed in a 20 mM potassium phosphate buffer (pH=6.6) containing 320 mM saccharose, 1 mM dithiothreitol and 50 μM NADPH (solution A) at 0° C., then purified and cut into pieces of 2 to 3 $mm^3$ size by shears. The chopped tissue was then homogenized at 0° C. in solution A having a 4 to 5-fold volume of the prostate in an Ultra turrax homogenizer (Janke and Kunkel, Ika-Werk), then the homogenate was rubbed through a plastic filter of 0.5 mm pore size. The thus obtained prostate suspension was further ground for 5 minutes by using supersound and the cell debris was purified by two ultracentrifugations (100000×g, 1 hour at 0° C.). The cell debris settling in the second centrifugation was suspended in a twofold tissue volume of 20 mM potassium phosphate buffer of 0° C. (pH=6.6) containing 20% of glycerol and 1 mM of dithiothreitol. Thereafter, the suspension was filtered through a plastic filter of 0.5 mm pore size and stored in divided portions at −70° C. until the use.

Measurement of the 5α-reductase Inhibition

In the routine investigation of enzyme inhibition, the reaction mixture contained 0.5 μM [$^3$H]-testosterone (with a specific activity of 2.7 GBq/mmol), 1 mM dithiothreitol, 500 μM NADPH, 40 mM TRIS citrate buffer (pH=5.1) and enzyme preparation containing 0.5 to 0.6 mg of protein in a volume of 0.5 ml. ["TRIS" is the abbreviation of tris(hydroxymethyl)aminomethane]. The substances under test dissolved in 5 μl of ethanol were added to the incubation system in an amount sufficient to reach a final concentration of $10^{-6}$ to $10^{-9}$M of the substances in the reaction mixture. The control samples also contained 5 μl of ethanol. After incubating the samples at 37° C. for 10 minutes (the enzyme reaction was linear for 20 minutes) the activity of the enzyme was stopped by adding 2 ml of ethyl acetate. Subsequently, the steroids (testosterone, DHT, androstanediol) were extracted with an organic solvent and then separated on a Poligram Sil G/UV 254 (Macherey Nagel) thin layer chromatography (TLC) sheet by using twofold development with a 198:3 mixture of chloroform/methanol. For visualizing the steroid spots on the TLC sheet, 12 μg of testosterone, DHT and androstanediol each were added to the samples during the extraction. After the TLC separation the steroid spots were cut out and the percentage conversion of testosterone to DHT and androstanediol (which latter is the chief metabolite of DHT) were determined on the bases of their radioactivity measured by liquid scintillation method. The 5α-reductase-inhibiting activity of the substances under test was characterized by their concentration ($IC_{50}$ value) decreasing the percentage conversion of testosterone by 50% in comparison to the control value.

In these investigations 17β-[N-(1,1-dimethylethyl)carbamoyl]-3-oxo-4-aza-5α-androst-1-ene (compound MK-906, Finasteride) developed by Merck Sharp and Dohme Company (United States) was used as reference substance. The results of the comparative tests are shown in the following Table.

TABLE

| Compound | $IC_{50}$ |
|---|---|
| 17β-[N-(1,1-Dimethylethyl)carbamoyl]-3-oxo-4-aza-5α-androst-1-ene (MK-906) | $1.84 \times 10^{-8}$ M |
| 17β-(2,6-Dimethylpiperidinocarbonyl)-3-oxo-4-aza-5α-androst-1-ene | $8.59 \times 10^{-9}$ M |
| 17β-(Hexamethyleneiminocarbonyl)-3-oxo-4-aza-5α-androst-1-ene | $1.31 \times 10^{-8}$ M |
| 17β-(Heptamethyleneiminocarbonyl)-3-oxo-4-aza-5α-androst-1-ene | $8.64 \times 10^{-9}$ M |

It can be seen from the data that the compounds of the formula (I) according to the invention posses a stronger 5α-reductase-inhibiting activity in comparison to 17β-[N-(1,1-dimethylethyl)carbamoyl]-3-oxo-4-aza-5α-androst-1-ene used as reference substance.

Based on their steroid 5α-reductase-inhibiting activity, the compounds of the formula (I) of the present invention are useful for the treatment of all diseases where the therapeutic aim is to decrease the tissue concentration of DHT. Diseases of such kind are, e.g., the benign prostatic hyperplasia, acne, seborrhea, female hirsutism and androgenic alopecia.

The compounds of the formula (I) of the invention can preferably be used for treating the benign prostatic hyperplasia. The compounds can be administered in various ways to the patients in order to achieve the effect desired. In connection with the treatment of benign prostatic hyperplasia, "patients" are meant to be warm-blooded male animals such as male dogs as well as male humans.

The compounds of the invention can be administered alone or in combination with other compounds. Preferably, the compounds can be administered in the form of pharmaceutical compositions in oral or parenteral, e.g., intravenous, intraperitoneal, intramuscular or subcutaneous routes including the direct injection of the active agent to the prostate. Pharmaceutical compositions as implants with sustained release may also be employed. The amount to be used of the compounds can be varied under wide limits and may be any effective amount. Depending on the patient to be treated, severity of the disease treated and route of the administration, the effective amount of the compounds may be about daily 0.001 to 10 mg/kg of body weight.

Pharmaceutical compositions useful for oral or parenteral administration may contain, e.g., 0.1 to 100 mg of a compound according to the invention. The dosage limits defined for the compounds of the invention are useful for diminishing the size of prostate, i.e., they represent an amount being effective for the treatment of benign prostatic hyperplasia. The compounds according to the invention can be used for the treatment of the developed disease (benign prostatic hyperplasia) or for treating the symptoms induced by the disease, respectively; however, they can be employed for a prophylactic therapy, too.

The compounds according to the invention can be used also for the treatment of acne, seborrhea, androgenic alopecia or female hirsutism. In these cases the compounds may be administered topically, orally, parenterally, e.g., intramuscularly or subcutaneously. It is suitable to employ a topical treatment. Here, the patients to be treated may be any mammal, e.g. primate, such as human and within this men or women. The compounds may be used alone or in combination with other compounds in the form of suitable pharmaceutical compositions. The amount to be used of the active agent depends on the manner of treatment, state of the patient as well as the severity of the disease (acne, seborrhea, androgenic alopecia, female hirsutism). For oral and parenteral administration the effective dose of the compound may be about daily 0.001 to 10 mg/kg of body-weight. In these routes of administration the pharmaceutical compositions may contain 0.1 to 100 mg of a compound of the invention as active ingredient. For topical administration the active ingredient content of the composition can be varied from 0.001% up to 5%. When administered topically, the active ingredient may be directly applied onto the site to be treated or onto the oral or nasal mucosa.

The invention also relates to a method for inhibiting the activity of the 5α-reductase enzyme in mammals including humans. This method comprises administering a therapeutically effective amount of active agent of the the formula (I) to the patient.

The invention is illustrated in detail by the following non-limiting Examples.

EXAMPLE 1

Preparation of 17-hydrazono-4-aza-5α-androstan-3-one

To a suspension of 10 g (0.0346 mol) of 4-aza-5α-androstane-3,17-dione in 100 ml of ethanol 14 ml (0.1 mol) of triethylamine and 50 ml (1.0 mol) hydrazine hydrate are added and the mixture is boiled under reflux for 3 hours. [The progress of the reaction is followed by thin layer chromatography (TLC)]. After complete reaction the mixture is cooled down, the solution is evaporated to one tenth of its original volume and then, the product is precipitated by adding about 10-fold volume of water. After compaction the precipitate is filtered, washed with water until neutral and dried to obtain the title compound in a yield of 9.44 g (90%), m.p.: 254°–258° C.

$^1$H-NMR (300 MHz, CDCl$_3$) δ ppm: 0.86 (s,3H,18-CH$_3$), 0.93 (s,3H,19-CH$_3$), 2.41 (m,2H,H-2), 3.07 (dd,1H,H-5), 4.77 (br,2H,NH$_2$), 5.74 (br,1H,NH).

EXAMPLE 2

Preparation of 17-hydrazono-4-azaandrost-5-en-3-one

The process of Example 1 is followed, except that 4-azaandrost-5-ene-3,17-dione is used as starting material to give the title compound in a yield of 35%, m.p.: 379°–382° C.

IR [KBr, ν(cm$^{-1}$)]: 1633 (C=C), 1661 (C=N), 1693 (C=O), 3200 (NH), 3350 (NH$_2$).

EXAMPLE 3

Preparation of 17-hydrazono-4-methyl-4-aza-5α-androstan-3-one

The process of Example 1 is followed, except that 4-methyl-4-aza-5α-androstane-3,17-dione is used as starting material to obtain the title compound in a yield of 75%, m.p.: 211°–218° C.

$^1$H-NMR (300 MHz, CDCl$_3$) δ ppm: 0.86 (s,3H,18-CH$_3$), 0.91 (s,3H,19-CH$_3$), 2.93 (s,3H,N-CH$_3$), 3.05 <dd(J=3.6;J=12.6),1H,H-5>, 4.78 (vbr, 2H, NH$_2$).

EXAMPLE 4

Preparation of 17-iodo-4-aza-5α-androst-16-en-3-one

A.)

After dissolving 9.1 g (0.03 mol) of 17-hydrazono-4-aza-5α-androstan-3-one in 1200 ml of an 1:1 chloroform/benzene mixture and then adding 90 ml of triethylamine, 11.4 g (0.045 mol) of iodine dissolved in 110 ml of benzene are dropwise added to the above solution, which is then stirred an additional 60–90 minutes at room temperature. (The progress of the reaction is followed by TLC method). After the reaction has become complete, the solution is diluted with 500 ml of chloroform, successively washed with 10% aqueous hydrochloric acid solution, water, 5% aqueous sodium thiosulfate solution, water, finally with 5% aqueous sodium hydrogen carbonate solution and water, then dried over anhydrous sodium sulfate. After evaporating the solvents under reduced pressure, the residue is purified by chromatography on a silica gel column by using chloroform and chloroform/acetone mixture as eluents. The product obtained is recrystallized from ethanol to give the title compound in a yield of 5.9 g (50%).

B.)

The preceding procedure is followed, except that tetramethylguanidine is used as base instead of triethylamine. In this way the title compound is produced in a yield of 65%, m.p.: 278°–282° C.

$^1$H-NMR (300 MHz, CDCl$_3$) δ ppm: 0.73 (s,3H,18-CH$_3$), (0.91 (s,3H,19-CH$_3$), 3.1 (dd,1H,H-5), 6.18 (m, 1H,H-16), 6.9 (br, 1H,NH).

EXAMPLE 5

Preparation of 17-iodo-4-azaandrosta-5,16-dien-3-one

The process of Example 4 A.) is followed, except that 17-hydrazono-4-azaandrost-5-en-3-one is used as starting substance to give the title compound in a yield of 57%, m.p.: 227°–230° C.

$^1$H-NMR (300 MHz, CDCl$_3$) δ ppm: 0.78 (s,3H,18-CH$_3$), 1.13 (s,3H,19-CH$_3$), 4.9 <dd(J=2.4; J=5.1),1H,H-6>, 6.15 <dd(J=3,2;J=1.7), 1H,H-16), 8.27 (br,1H,NH).

EXAMPLE 6

Preparation of 17-iodo-4-methyl-4-aza-5α-androst-16-en-3-one

The process of Example 4 A.) is followed, except that 17-hydrazono-4-methyl-4-aza-5α-androstan-3-one is used as starting substance and benzene is used as solvent to obtain the title compound in a yield of 52% m.p.: 176°–181° C.

$^1$H-NMR (300 MHz, CDCl$_3$) δ ppm: 0.74 (s,3H,18-CH$_3$), 0.92 (s,3H,19-CH$_3$), 2.94 (s,3H,N-CH$_3$), 3.07 <dd (J=3.7; J=12.6), 1H,H-5>, 6.13 <dd(J=3.2; J=1.7),1H,H-16).

EXAMPLE 7

Preparation of 17-chloro-4-methyl-4-aza-5α-androst-16-en-3-one

After dissolving 4 g (0.0126 mol) of 17-hydrazono-4-methyl-4-aza-5α-androstan-3-one in 40 ml of anhydrous pyridine and cooling down the solution to 0° C., a solution of 3.2 g (0.024 mol) of N-chlorosuccinimide dissolved in 40 ml of pyridine are added dropwise under vigorous stirring. After cessation of the violent nitrogen evolution, the reaction mixture is stirred an additional 15 minutes and then dropped into 800 ml of water. After compaction of the precipitate the crude product is filtered off, washed with water until neutral and dried over phosphorus pentoxide at room temperature under reduced pressure. The crude product obtained is purified by chromatography on a silica gel column by using chloroform as eluent. After recrystallization of the evaporation residue from petroleum ether, the title compound is obtained in a yield of 2.15 g (53%), m.p.: 139°–140° C.

$^1$H-NMR (60 MHz, CDCl$_3$) δ ppm: 0.88 (s,3H,18-CH$_3$), 0.93 (s,3H,19-CH$_3$), 2.89 (s,3H,N-CH$_3$), 3.0 (dd,1H,H-5), 5.53 (m,1H,H-16).

EXAMPLE 8

Preparation of 17-bromo-4-methyl-4-aza-5α-androst-16-en-3-one

The process of Example 7 is followed, except that similarly, 17-hydrazono-4-methyl-4-aza-5α-androstan-3-one is used as starting substance but N-bromosuccinimide is employed as reagent to obtain the title compound in a yield of 55%, m.p. 159°–161° C.

$^1$H-NMR (60 MHz, CDCl$_3$) δ ppm: 0.82 (s,3H,18-CH$_3$), 0.91 (s,3H,19-CH$_3$), 2.86 (s,3H,N-CH$_3$), 3.0 (dd, 1H,H-5), 5.68 (m, 1H,H-16).

EXAMPLE 9

Preparation of 17β-(2,6-dimethylpiperidinocarbonyl)-3-oxo-4-aza-5α-androst-16-ene After dissolving 3.99 g (0.01 mol) of 17-iodo-4-aza-5α-androst-16-en-3-one in 150 ml of dimethylformamide, 0.224 g (0.001 mol) of palladium(II) diacetate, 0.524 g (0.002 mol) of triphenylphosphine, 10 ml of triethylamine and 18.9 ml (0.14 mole) of cis-2,6-dimethylpiperidine are added to the above solution which is then maintained under a carbon monoxide atmosphere at 60° C. for 1.5 to 2 hours. (The progress of the reaction is followed by TLC and gas chromatography.) After complete progress of the reaction the amines and dimethylformamide (abbreviated: DMF) are distilled off under reduced pressure, the residue is dissolved in 150 ml of chloroform and successively washed with water, 5% aqueous hydrochloric acid solution, saturated aqueous sodium hydrogen carbonate solution and finally with saturated aqueous saline solution until neutral. The chloroform solution is dried over anhydrous sodium sulfate and after filtering off the drying agent and evaporating the solvent, the residue is purified by chromatography on a silica gel column by using ethyl acetate as eluent to obtain the title compound in a yield of 3.50 g (85%), m.p.: 307°–309° C.

$^1$H-NMR (60 MHz, CDCl$_3$) δ ppm: 0.94 (s,3H,19-CH$_3$); 1.09 (s,3H,18-CH$_3$); 1.24 (d,6H,CH-CH$_3$); 2.04 and 2.23 (2*m,2H,H-15); 2.40 (m,2H,H-2); 3.07 (dd,1H,H-5); 3.95–5.05 (vbr,2H,NCH-CH$_3$); 5.70 (m,1H,H-16); 6.20 (br, 1H,NH).

EXAMPLE 10

Preparation of 17β-(2,5-dimethylpyrrolidinocarbonyl)-3-oxo-4-aza-5α-androst-16-ene The process of Example 9 is followed by using 17-iodo-4-aza-5α-androst-16-en-3-one as starting substance and 2,5-dimethylpyrrolidine as reactant to obtain the title compound in a yield of 95%, m.p.: 281°–286° C.

EXAMPLE 11

Preparation of 17β-(heptamethyleneiminocarbonyl)-3-oxo-4-aza-5α-androst-16-ene The process of Example 9 is followed by using 17-iodo-4-aza-5α-androst-16-en-3-one as starting substance with heptamethyleneimine as reactant to give the title compound in a yield of 88%, m.p.: 282°–285° C.

EXAMPLE 12

Preparation of 17β-(2,6-dimethylpiperidinocarbonyl)-3-oxo-4-aza-5α-androstane After dissolving 2 g (0.0048 mol ) of 17β-(2,6-dimethylpiperidinocarbonyl)-3-oxo-4-aza-5α-androst -16-ene in 80 ml of formic acid, a suspension containing 2 g of charcoal-supported palladium catalyst in 12 ml of water is added under nitrogen and the heterogeneous reaction mixture is stirred at room temperature for 4 to 5 hours. (The progress of the reduction is followed by TLC method.) After complete progress of the reaction the catalyst is filtered off and washed with an 1:1 mixture of chloroform and methanol. After evaporating the combined solution to dryness, the residue is thoroughly triturated with water, the precipitate is filtered and washed with water to give the title compound in a yield of 1.74 g (87%), m.p.: 300°–303° C.

The title compound has been prepared also by hydrogenating 17β-(2,6-dimethylpiperidinocarbonyl)-3-oxo-4-azaandrosta-5,16-diene as described above to obtain a yield of 70%.

$^1$H-NMR (300 MHz, CDCl$_3$) δ ppm: 0.71 (s,3H,18-CH$_3$); 0.90 (s,3H,19-CH$_3$); 1.18 and 1.20 (2*d,6H,CH-CH$_3$); 2.40 (m,2H,H-2); 2.71 (t,1H,H-17); 3.04 (dd,1H,H-5); 4.28 and 4.73 (2*m,2H,NCH-CH$_3$); 6.12 (br,1H,NH).

EXAMPLE 13

Preparation of 17β-(2,5-dimethylpyrrolidinocarbonyl)-3-oxo-4-aza-5α-androstane A solution containing 2 g (0.005 mol) of 17β-(2,5-dimethylpyrrolidinocarbonyl)-3-oxo-4-aza-5α-androst-16-ene in 140 ml of ethanol is hydrogenated in the presence of 0.5 g of charcoal supported palladium catalyst under atmospheric pressure for 5 to 8 hours. (The progress of the reaction is followed by TLC method.) After complete hydrogenation and filtering off the catalyst, the solution is evaporated to give 1.9 g (95%) of the title compound, m.p.: 295°–300° C.

¹H-NMR (300 MHz, CDCl₃) δ ppm: 0.79 (s,3H,18-CH₃); 0.90 (s,3H,19-CH₃); 1.18 and 1.31 (2*d,6H,CH-CH₃); 2.40 (m,2H,H-2); 2.53 (t,1H,H-17); 3.05 (dd,1H,H-5); 4.11 (m,2H,NCH-CH₃); 6.27 (br,1H,NH).

EXAMPLE 14

Preparation of 17β-(heptamethyleneiminocarbonyl)-3-oxo-4-aza-5α-androstane

The process of Example 13 is followed, except that 17β-(heptamethyleneiminocarbonyl)-3-oxo-4-aza-5α-androst-16-ene is used as starting substance to obtain the title compound in a yield of 85%, m.p.: 256°–266° C.

¹H-NMR (60 MHz, CDCl₃) δ ppm: 0.82 (s,3H,18-CH₃); 0.91 (s,3H,19-CH₃); 2.8–4.1 (m,5H,H-5 and NCH₂); 6.69 (br,1H,NH).

EXAMPLE 15

Preparation of 17β-(hexamethyleneiminocarbonyl)-3-oxo-4-aza-5α-androstane

The process of Example 13 is followed, except that 17β-(hexamethyleneiminocarbonyl)-3-oxo-4-aza-5α-androst-16-ene is used as starting substance to give the title compound in a yield of 86%, m.p.: 276°–281° C.

EXAMPLE 16

Preparation of 17β-(4-methylpiperidinocarbonyl)-3-oxo-4-aza-5α-androstane

The process of Example 12 is followed, except that 17β-(4-methylpiperidinocarbonyl)-3-oxo-4-aza-5α-androst-16-ene is used as starting substance to obtain the title compound in a yield of 83%, m.p.: 314°–319° C.

EXAMPLE 17

Preparation of 17β-(2,6-dimethylpiperidinocarbonyl)-3-oxo-4-aza-5α-androst-1-ene To a suspension containing 2.07 g (0.005 mol) of 17β-(2,6-dimethylpiperidinocarbonyl)-3-oxo-4-aza-5α-androstane in 24 ml of toluene, 1.25 g (0.0055 mol) of 2,3-dichloro-5,6-dicyano-1,4-benzoquinone are portionwise added during 30 minutes, then the reaction mixture is stirred under nitrogen an additional 30 minutes. Subsequently, 5.5 ml (0.021 mol) of bis(trimethylsilyl)-trifluoroacetamide are dropwise added to the suspension during 20 to 30 minutes and after termination of the portionwise addition, 2 drops of trifluoroacetic acid are added, then the mixture is stirred at room temperature for 20 hours. (The progress of the reaction is followed by TLC method.) After complete progress of the reaction 0.05 g (0.0005 mol) of 1,3-cyclohexanedione are added to the reaction mixture which is then stirred at room temperature an additional 3 hours and subsequently boiled under reflux for 18 to 20 hours. After diluting with 6 ml of methylene chloride, the reaction mixture is washed with sodium hydrogen carbonate solution, dried over anhydrous sodium sulfate and the solvents are removed under reduced pressure. After recrystallization of the residue from ethyl acetate the title compound is obtained in a yield of 1.44 g (70%), m.p.: 288°–292° C.

¹H-NMR (300 MHz, CDCl₃) δ ppm: 0.72 (s,3H,18-CH₃); 0.97 (s,3H,19-CH₃); 1.19 and 1.21 (2,d,6H,CH-CH₃); 2.73 (t,1H,H-17); 3.32 (m,1H,H-5); 4.28 and 4.73 (2*m,2H, NCH-CH₃); 5.80 (dd,1H,H-2); 6.02 (br,1H,NH); 6.77 (d,1H, H-1).

EXAMPLE 18

Preparation of 17β-(2,5-dimethylpyrrolidinocarbonyl)-3-oxo-4-aza-5α-androst-1-ene The process of Example 17 is followed, except that 17β-(2,5-dimethylpyrrolidinocarbonyl)-3-oxo-4-aza-5α-androstane is used as starting substance to give the title compound in a yield of 67%, m.p.: 291°–295° C.

¹H-NMR (300 MHz, CDCl₃) δ ppm: 0.80 (s,3H,18-CH₃); 0.97 (s,3H,19-CH₃); 1.19 and 1.31 (2*d, 6H,CH-CH₃); 2.54 (t,1H,H-17); 3.32 (m,1H, H-5); 4.12 (m,2H,NCH-CH₃); 5.80 (dd,1H,H-2); 6.03 (br,1H,NH); 6.77 (d,1H,H-1).

EXAMPLE 19

Preparation of 17β-(heptamethyleneiminocarbonyl)-3-oxo-4-aza-5α-androst-1-ene

The process of Example 17 is followed, except that 17β-(heptamethyleneiminocarbonyl)-3-oxo-4-aza-5α-androstane is used as starting substance to obtain the title compound in a yield of 72%, m.p.: 278°–281° C.

¹H-NMR (60 MHz, CDCl₃) δ ppm: 0.82 (s,3H,18-CH₃); 0.98 (s,3H,19-CH₃); 2.66 (t,1H,H-17); 3.32 (m,5H,H-5); 3.07–3.3 and 3.63–3.86 (m,4H,NCH₂); 5.80 (dd,1H,H-2); 6.02 (br,1H,NH); 6.78 (d,1H,H-1).

EXAMPLE 20

Preparation of 17β-(hexamethyleneiminocarbonyl)-3-oxo-4-aza-5α-androst-1-ene

The process of Example 17 is followed, except that 17β-(hexamethyleneiminocarbonyl)-3-oxo-4-aza-5α-androstane is used as starting substance to obtain the title compound in a yield of 71%, m.p.: 270°–273° C.

¹H-NMR (60 MHz, CDCl₃) δ ppm: 0.81 (s,3H,18-CH₃); 0.98 (s,3H,19-CH₃); 2.9–4.1 (m,5H,H-5 and NCH₂); 5.79 (dd,1H,H-2); 6.5 (br,1H,NH); 6.79 (d,1H,H-1).

EXAMPLE 21

Preparation of 17β-(4-methylpiperidinocarbonyl)-3-oxo-4-aza-5α-androst-1-ene

The process of Example 17 is followed, except that 17β-(4-methylpiperidinocarbonyl)-3-oxo-4-aza-5α-androstane is used as starting substance to give the title compound in a yield of 75%, m.p.: 318°–324° C.

EXAMPLE 22

Preparation of 17β-(3,3-dimethylpiperidinocarbonyl)-3-oxo-4-aza-5α-androst-1-ene The process of Example 17 is followed, except that 17β-(3,3-dimethylpiperidinocarbonyl)-3-oxo-4-aza-5α-androstane is used as starting substance to obtain the title compound in a yield of 73%, m.p.: 278°–282° C.

EXAMPLE 23

Preparation of 17β-(4,4-pentamethylenepiperidinocarbonyl)-3-oxo-4-aza-5α-androst-1-ene The process of Example 17 is followed, except that 17β-(4,4-pentamethylenepiperidinocarbonyl)-3-oxo-4-aza-5α-androstane is used as starting substance to give the title compound in a yield of 75%, m.p.: 308°–311° C.

EXAMPLE 24

Preparation of 17β-(2,6-dimethylpiperidinocarbonyl)-3-oxo-4-aza-5α-androsta-1,16-diene The process of Example 17 is followed, except that 17β-(2,6-dimethylpiperidinocarbonyl)-3-oxo-4-aza-5α-androst-16-ene is used as starting substance to give the title compound in a yield of 62%, m.p.: 288°–290° C.

$^1$H-NMR (300 MHz, CDCl$_3$) δ ppm: 1.01 (s,3H,19-CH$_3$); 1.10 (s,3H,18-CH$_3$); 1.24 and 1.25 (2*d,6H,CH-CH$_3$); 2.05 and 2.23 (2*m,2H,H-15); 3.35 (m, 1H,H-5); 4.00–5.1 (vbr, 2H,NCH-CH$_3$); 5.71 (m,1H,H-16); 5.80 (dd,1H,H-2); 6.19 (br,1H,NH); 6.80 (d,1H,H-1).

EXAMPLE 25

Preparation of 17β-(2,5-dimethylpyrrolidinocarbonyl)-3-oxo-4-aza-5α-androsta-1,16-diene The process of Example 17 is followed, except that 17β-(2,5-dimethylpyrrolidinocarbonyl)-3-oxo-4-aza-5α-androst-16-ene is used as starting substance to obtain the title compound in a yield of 57%, m.p.: 284°–287° C.

$^1$H-NMR (300 MHz, CDCl$_3$) δ ppm: 1.01 (s,3H,19-CH$_3$); 1.12 (s,3H,18-CH$_3$); 1.22 and 1.29 (2*d,6H,CH-CH$_3$); 2.05 and 2.24 (m,2H, H-15); 3.35 (m,1H,H-5); 3.95–4.18 (m,2H, NCH-CH$_3$); 5.82 (dd,1H,H-2); 5.87 (m,1H,H-16); 6.24 (br, 1H,NH); 6.81 (d,1H,H-1).

EXAMPLE 26

Preparation of 17β-(2,6-dimethylpiperidinocarbonyl)-4-methyl-3-oxo-4-aza-5α-androstane The process of Example 13 is followed, except that 17β-(2,6-dimethylpiperidinocarbonyl)-4-methyl-3-oxo-4-aza-5α-androst-16-ene is used as starting substance to obtain the title compound in a yield of 88%, m.p.: 200°–203° C.

$^1$H-NMR (60 MHz, CDCl$_3$) δ ppm: 0.71 (s,3H,18-CH$_3$); 0.90 (s,3H,19-CH$_3$); 1.21 (d,6H,CH-CH$_3$); 2.92 (s,3H, NCH$_3$); 3.05 (dd,1H,H-5); 4.0–5.0 (2*vbr,2H,2*NCH-CH$_3$); 6.12 (br, 1H,NH).

EXAMPLE 27

Preparation of 17β-(heptamethyleneiminocarbonyl)-4-methyl-3-oxo-4-aza-5α-androstane The process of Example 13 is followed, except that 17β-(heptamethyleneiminocarbonyl)-4-methyl-3-oxo-4-aza-5α-androst-16-ene is used as starting substance to give the title compound in a yield of 85%, m.p.: 126°–129° C.

$^1$H-NMR (60 MHz, CDCl$_3$) δ ppm: 0.83 (s,3H,18-CH$_3$); 0.91 (s,3H,19-CH$_3$); 2.94 (s,3H,NCH$_3$); 2.8–4.1 (m,5H,H-5 and NCH$_2$).

EXAMPLE 28

Preparation of 17β-(hexamethyleneiminocarbonyl)-4-methyl-3-oxo-4-aza-5α-androstane The process of Example 13 is followed, except that 17β-(hexamethyleneiminocarbonyl)-4-methyl-3-oxo-4-aza-5α-androst-16-ene is used as starting substance to obtain the title compound in a yield of 87%, m.p.: 135°–137° C.

$^1$H-NMR (60 MHz, CDCl$_3$) δ ppm: 0.80 (s,3H,18-CH$_3$); 0.91 (s,3H,19-CH$_3$); 2.94 (s,3H,NCH$_3$); 2.8–4.1 (m,5H,H-5 and NCH$_2$).

EXAMPLE 29

Preparation of an Oily Injectable Solution

The active ingredient is dissolved in the mixture of benzyl benzoate and castor oil suitable for preparing injectable solution, then the solution is filled up to the desired volume with castor oil. Subsequently, the solution is filtered until free from bacteria and strange materials, then filled into ampoules and sterilized by heat.

The components of a composition of 1 ml volume are as follows:

| | |
|---|---|
| Active ingredient | 50 mg |
| Benzyl benzoate | 120 mg |
| Castor oil filled up to | 1 ml. |

Instead of castor oil sunflower oil may also be used with the same result.

What is claimed is:

1. A compound of the Formula (I)

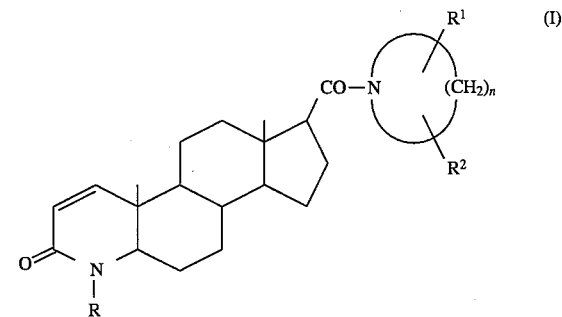

wherein
R is hydrogen;
R$^1$ and R$^2$ are each methyl or one of R$^1$ or R$^2$ is hydrogen and the other is methyl; and n is 4 or 5.

2. The compound of the Formula (I) defined in claim 1 selected from the group consisting of:

17beta-(4-methylpiperidinocarbonyl)-3-oxo-4-aza-5alpha-androst-1-ene;

17beta-(3,3-dimethylpiperidinocarbonyl)-3-oxo-4-aza-5alpha-androst-1-ene; and 17-beta-(2,6-dimethylpiperidinocarbonyl)-3-oxo-4-aza-5alpha-androst-1-ene.

3. The compound of the Formula (I) defined in claim 1 which is 17beta-(4-methylpiperidinocarbonyl)-3-oxo-4-aza-5alpha-androst-1-ene.

4. A pharmaceutical composition with 5 alpha reductase enzyme inhibiting effect which comprises as active ingredient effective amount of a compound of the Formula (I) as defined in claim 1 in admixture with a pharmaceutically acceptable inert carrier.

5. A method for treating acne in a mammalian subject which comprises the step of administering to said subject an anti-acne effective amount of a compound of the Formula (I) as defined in claim 1.

* * * * *